(12) United States Patent
Jamshidi

(10) Patent No.: US 8,663,282 B2
(45) Date of Patent: Mar. 4, 2014

(54) ADVANCED INTRA-SPINAL DECOMPRESSION IMPLANT

(71) Applicant: Saied Jamshidi, Potomac, MD (US)

(72) Inventor: Saied Jamshidi, Potomac, MD (US)

(73) Assignee: Saied Jamshidi, Potomac, MD (US)

( * ) Notice: Subject to any disclaimer, the term of this patent is extended or adjusted under 35 U.S.C. 154(b) by 0 days.

(21) Appl. No.: 13/902,930

(22) Filed: May 27, 2013

(65) Prior Publication Data

US 2013/0261749 A1 Oct. 3, 2013

Related U.S. Application Data

(63) Continuation-in-part of application No. 13/565,896, filed on Aug. 3, 2012, now Pat. No. 8,449,575, which is a continuation-in-part of application No. 12/245,717, filed on Oct. 4, 2008, now Pat. No. 8,236,030.

(51) Int. Cl.
*A61B 17/70* (2006.01)
*A61B 17/58* (2006.01)
*A61B 17/60* (2006.01)
*A61F 2/00* (2006.01)

(52) U.S. Cl.
USPC .............................................. 606/246; 606/90

(58) Field of Classification Search
USPC .......................................... 606/90, 246–253
See application file for complete search history.

(56) References Cited

U.S. PATENT DOCUMENTS 5,772,661 A 6/1998 Michelson

*Primary Examiner* — Sameh Boles
(74) *Attorney, Agent, or Firm* — MaxValueIP LLC

(57) ABSTRACT

A new intra-spinal decompression implant is introduced. One example for our presentation is a device with 2 or 3 pieces, with each piece with 2 clamps, symmetrically located on each side of each piece. The main piece has at least 2 screws which engage into 2 or more grooves in the side piece, to get attached to the side piece. The $3^{rd}$ piece, as an optional piece, is the bottom piece, which is similar to the side piece, and gets attached to the main piece, using same or different screws. Each piece is attached to the human body, during back surgery, with corresponding clamps. This improves the quality of the surgery and the result for the patient. More examples are given here.

20 Claims, 15 Drawing Sheets

ADVANCED INTRA-SPINAL DECOMPRESSION IMPLANT

RELATED APPLICATIONS

This application is a CIP (continuation-in-part) of another co-pending application, application Ser. No. 13/565,896, filed Aug. 3, 2012, now allowed, with the similar title and same inventor, and it claims priority to that parent application, and it incorporates all the parent's teachings by reference. The Ser. No. 13/565,896 is in turn a CIP (continuation-in-part) of another application, now the U.S. Pat. No. 8,236,030, filed Oct. 4, 2008, with the similar title and same inventor, and it claims priority to that parent application, and it incorporates all the parent's teachings by reference.

BACKGROUND OF THE INVENTION

An Intra-spinal decompression implant comprises of two plate attachments to a titanium metal implant that fits between the spinous processes of the vertebrae in the lower back, decompressing the neuro elements. These devices are implanted without fixation to the bone or ligament to preserve physiological spinal motion. These devices are particularly useful for patients who suffer from degenerative disc disease, spinal stenosis, or lateral recess syndrome. Such device has many advantages, including easy installation and therefore capable of decompressing the spinal canal and nerve roots quickly and efficiently.

The Intra-spinal decompression implants available to date in the market require different size of side plates and/or different size of implant body for different spinal levels or different patients. They are also prone to moving from the intended location. The following Website provides a good description of one the available Intra-spinal decompression implants in the market: http://www.ispub.com/ostia/index.php?xmlFilePath=journals/ijmist/vol1n1/xstop.xml This invention provides multiple improved designs and devices for Intra-spinal decompression implants that unlike other decompression implants on the market can be used on multiple spinal levels and different type of patients. The invented devices or systems will reduce surgery time by almost half an hour per spinal level and allows for the procedure to be done on local standby and on an out-patient basis, reducing the risk and cost, which are very beneficial to all.

SUMMARY OF THE INVENTION

One embodiment of the present invention is a device with 2 or 3 pieces, with each piece with 2 clamps, symmetrically located on each side of each piece. The main piece has at least 2 screws which engage into 2 or more grooves in the side piece, to get attached to the side piece. The 3$^{rd}$ piece, as an optional piece, is the bottom piece, which is similar to the side piece, and gets attached to the main piece, using same or different screws. Each piece is attached to the human body, during back surgery, with corresponding clamps.

In one embodiment, the materials used for clamps, pieces, and screws can be selected from a variety of composites, plastics, metal, alloy, and the like, which are durable, non-toxic, non-reactionary with the tissues (for allergy or rejection possibility by the body), reasonably priced, and/or easily manufactured. The clamps can be from the same materials as the pieces. The pieces may or may not be from the same materials. The clamps can be molded as one piece as the piece it is attached with.

One embodiment of the present invention is an Intra-spinal decompression implant that comprises of two plate attachments to a titanium metal implant that fits between the spinous processes of the vertebrae in the lower back, decompressing the neuro elements. The invention (as an example) has a number of new design features, including:
  Lateral and vertical side plate adjustments
  An implant body capable of dual axis adjustment with a large cavity for packing of bone graft material, for tissue to fuse around and inside the device, for better installation (the cavity can be multiple cavities, in middle, and small ones on the sides, as one example)
  The implant body design incorporates a stepped and pointed conical tipped end, for better installation
  Conical piercing tipped studs for attachment to the vertebrae
  The implant design incorporates precision-machined slots and keys in the implant body and side plates

DETAILED DESCRIPTION OF THE PREFERRED EMBODIMENTS

Figure 1:
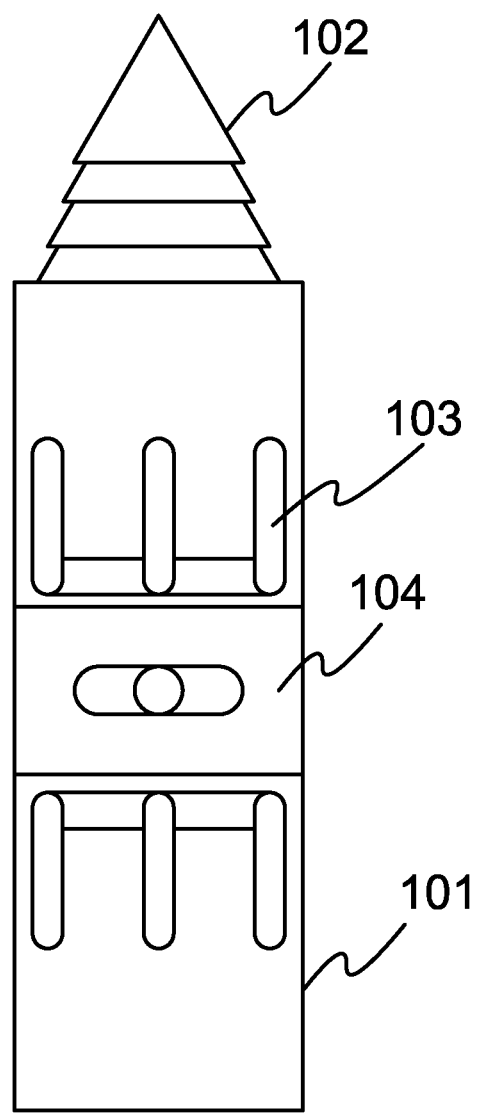
FIG. 1 is the top view of the implant body that incorporates a stepped and pointed conical tipped end.
Figure 2:
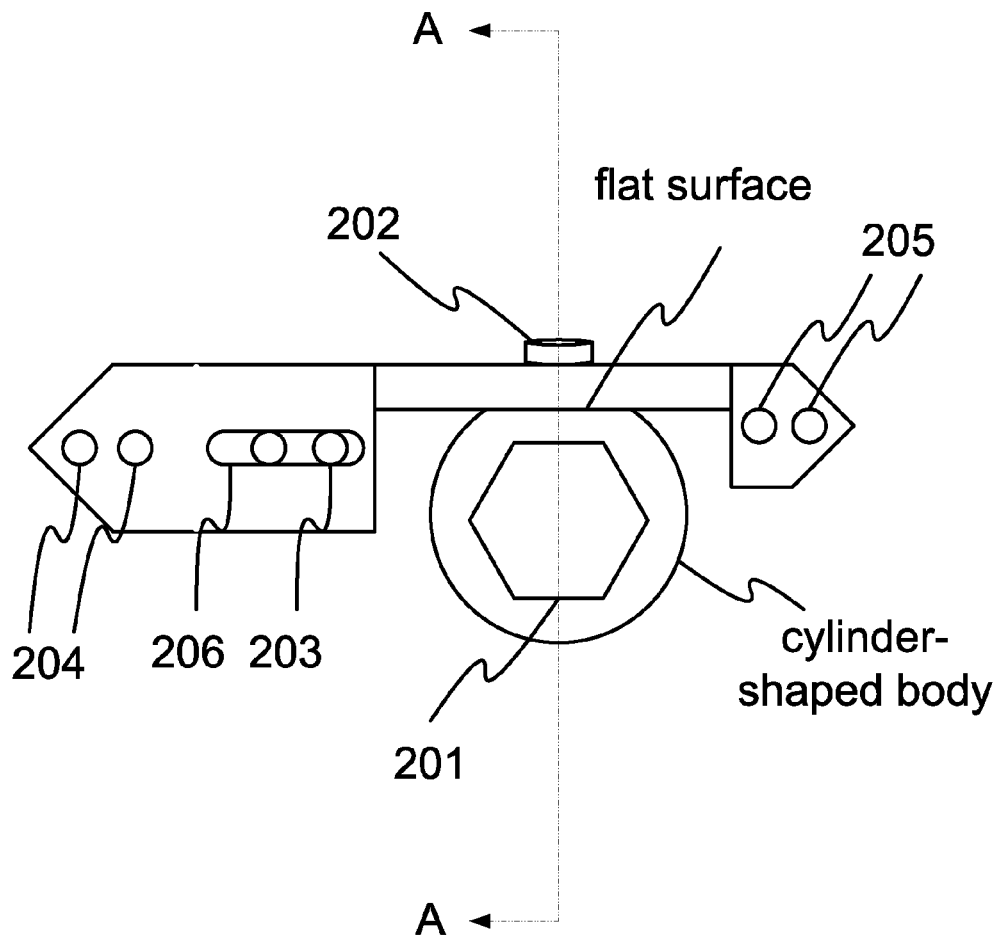
FIG. 2 illustrates one of the side plate attachments to the implant body, with rear and front parts, in which the length of the front part is adjustable.
Figure 3:
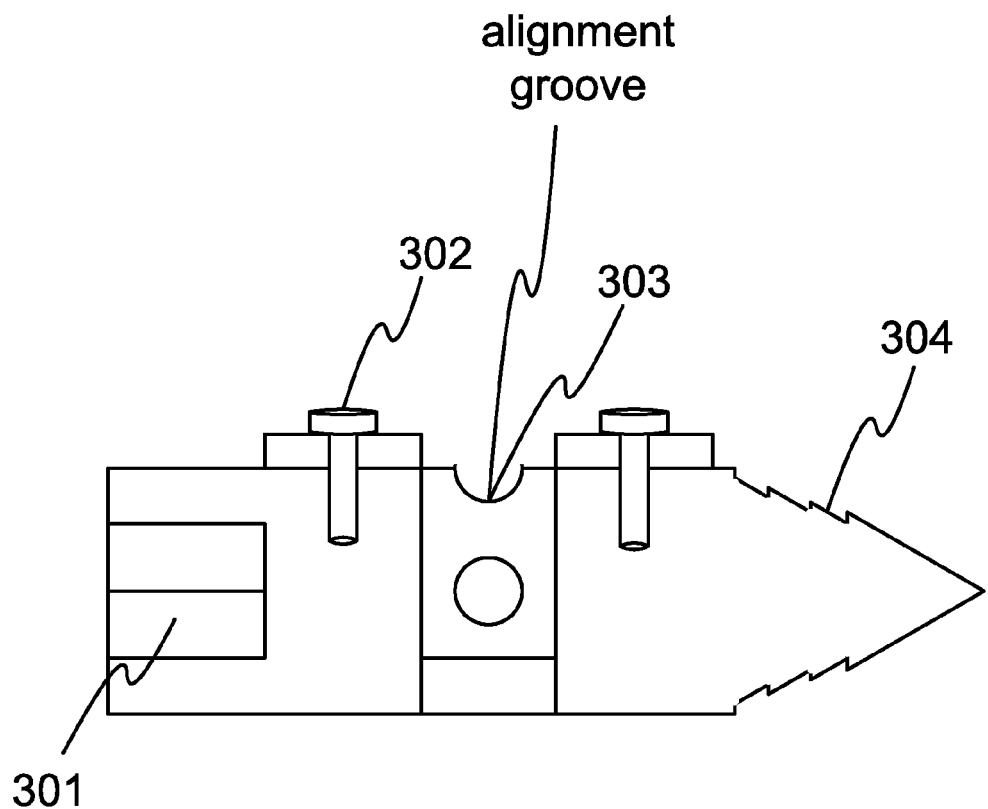
FIG. 3 is a cross section view of the implant body, which shows how the side plate is attached to the implant body as well as the bottom cavity of the implant body.
Figure 4:
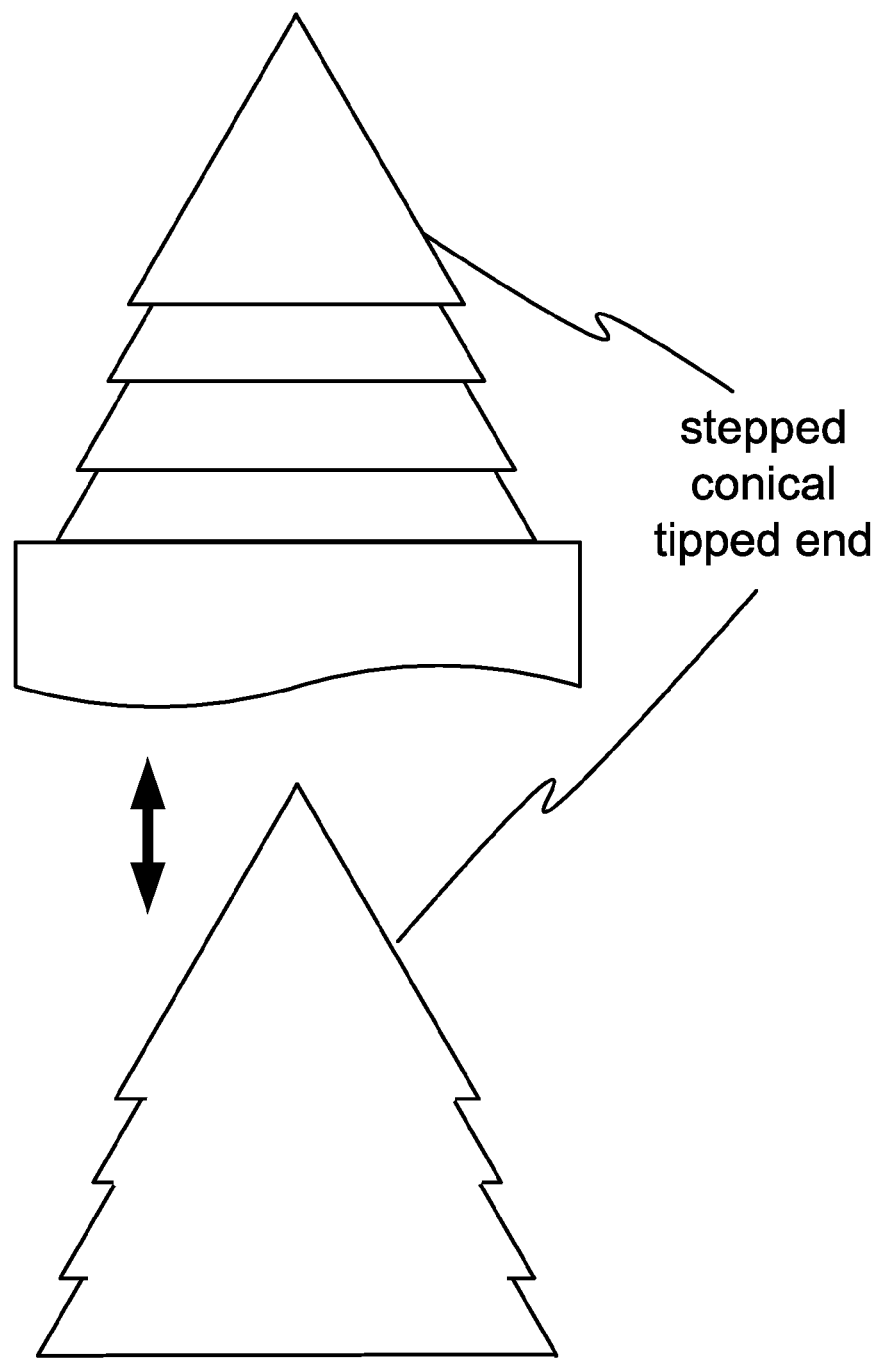
FIG. 4 shows the stepped and conical ripped end and its cross section.
Figure 5:
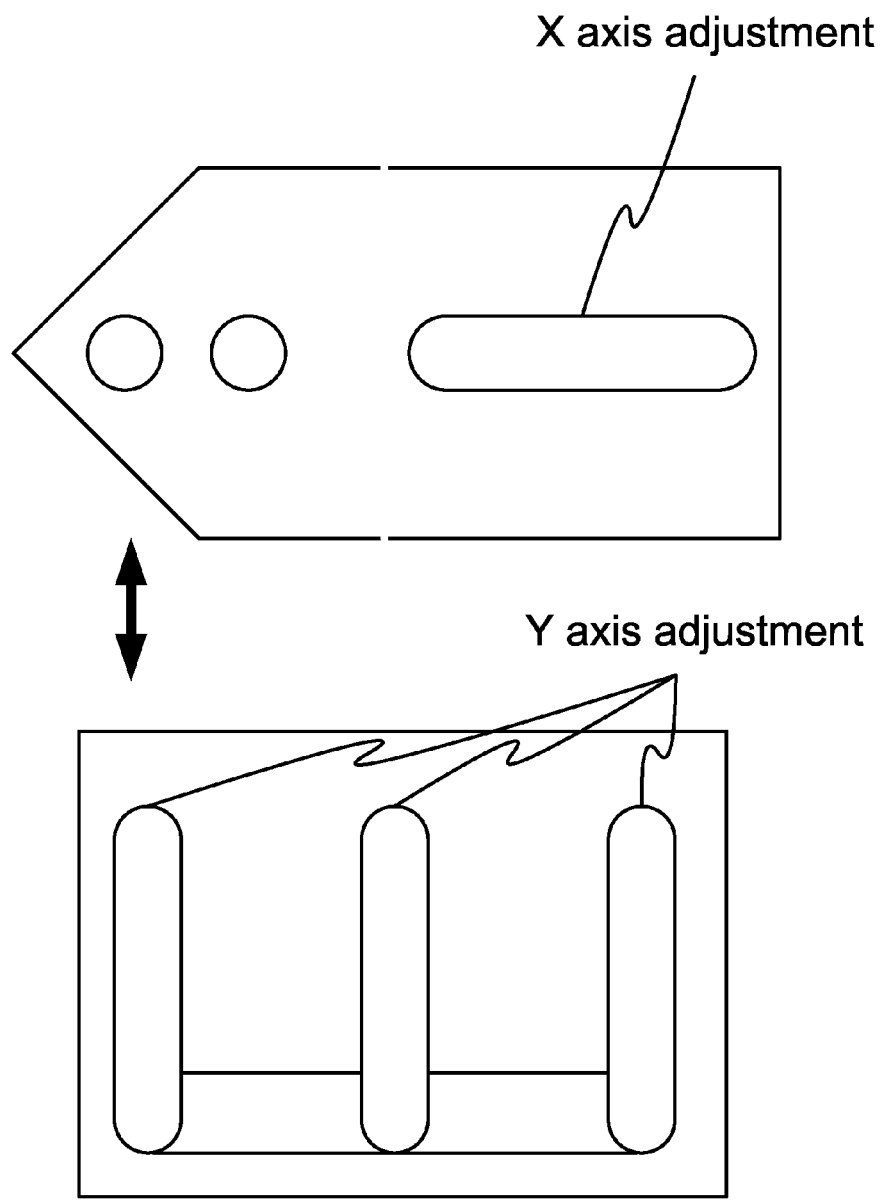
FIG. 5 shows the dual axis (X and Y) adjustment mechanisms of the implant.

The Intra-spinal decompression implant of the preferred embodiment is shown in FIGS. 1, 2 and 3. It is designed for plate attachment to the titanium metal implant and fits between the spinous processes of the vertebrae in the lower back, decompressing the neuro elements. It is designed to remain safely and permanently in place as the spinal processes gradually fuses together while the spine naturally repairs itself. The device is particularly useful for patients who suffer from degenerative disc disease, spinal stenosis, or lateral recess syndrome. The device has many advantages, including easy installation and therefore capable of decompressing the spinal canal and nerve roots quickly and inefficiently. Unlike other decompression implants on the market, the side plates of the device are adjustable in two dimensions (FIG. 5), which allow them to be universally used on multiple spinal levels or different patients. The device will reduce surgery time by almost half an hour per spinal level and allows for the procedure to be done on local standby and on an out-patient basis.

Figure 9:
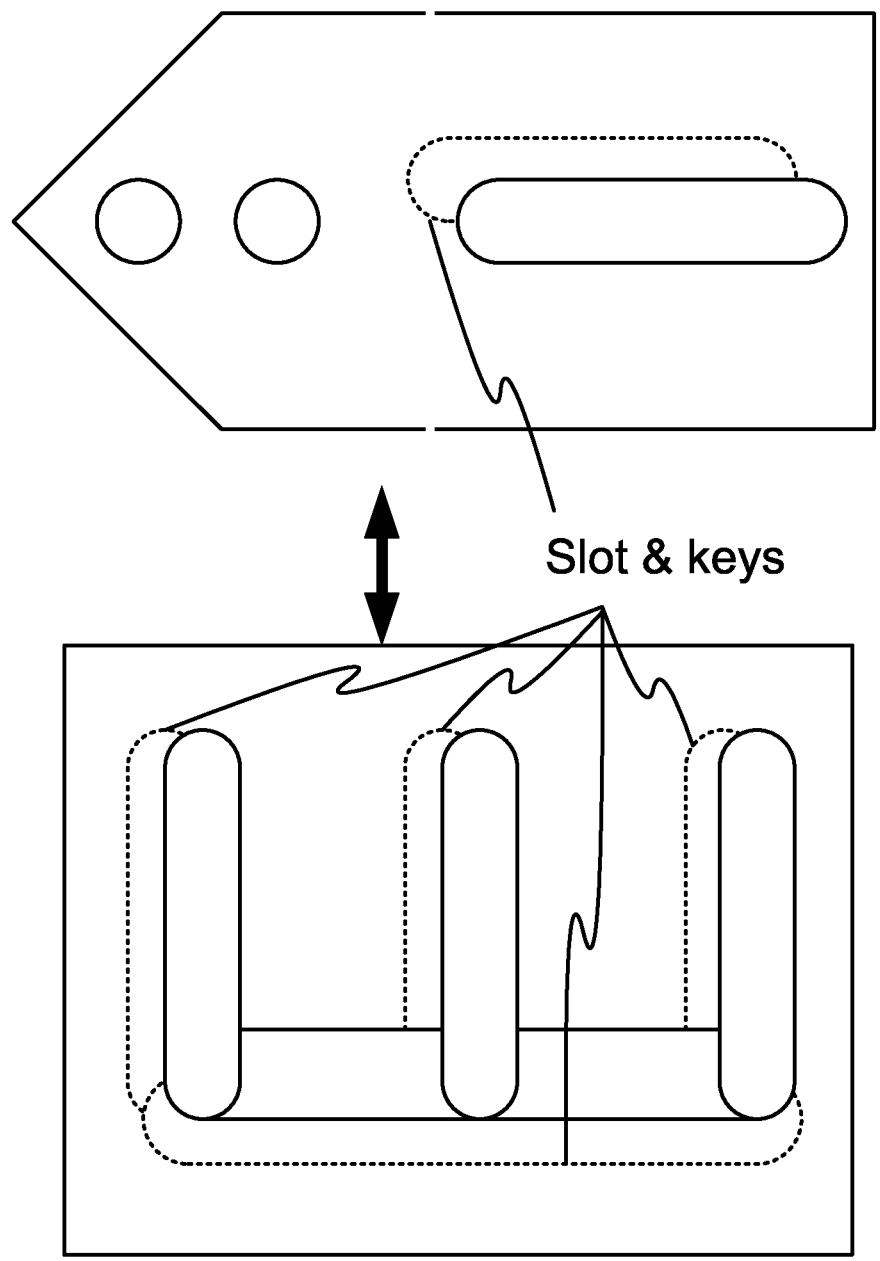
FIG. 9 shows the slot and key mechanism used for dual axis adjustment of the implement.
Figure 10:
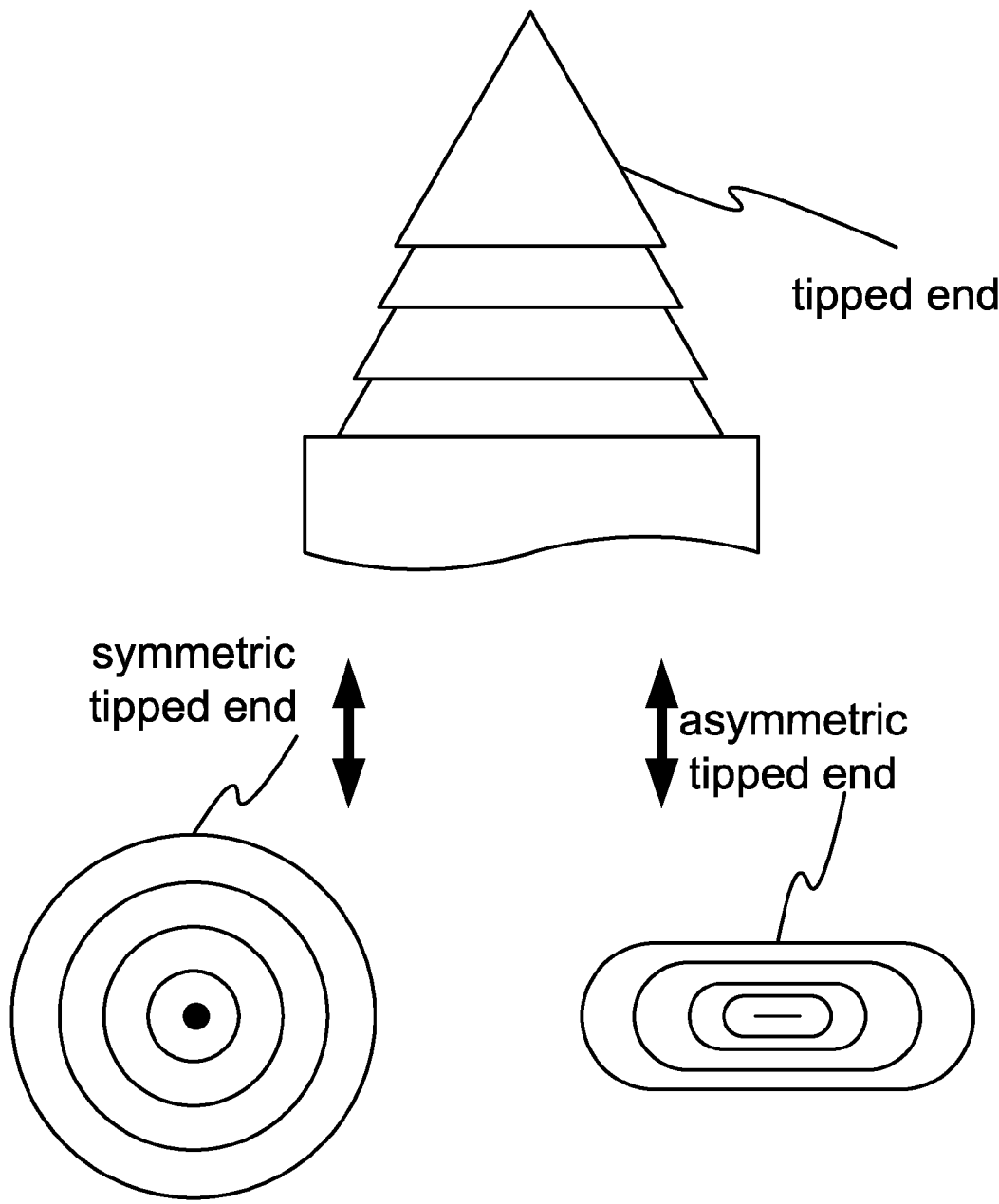
FIG. 10 shows a symmetric and an asymmetric stepped tipped end of the implant body.

The design includes implant adjustments in width and length to accommodate the patient anatomy. Height adjustment is accomplished by replacement of the implant body to a different diameter (larger or smaller size). The side plates are universal and can be assembled with a variety of sizes. Lateral and vertical adjustment (length and width) is accomplished by means of slots and keys (FIG. 9) that are machined in the side plate and implant body.

Please note that Appendices 1-5, 6-7, and 8-31 show various components, installations, usages, and viewpoints of our system, in different embodiments, for different applications. These are our own teachings for support of our spec and claims.

Design Features

Figure 6:
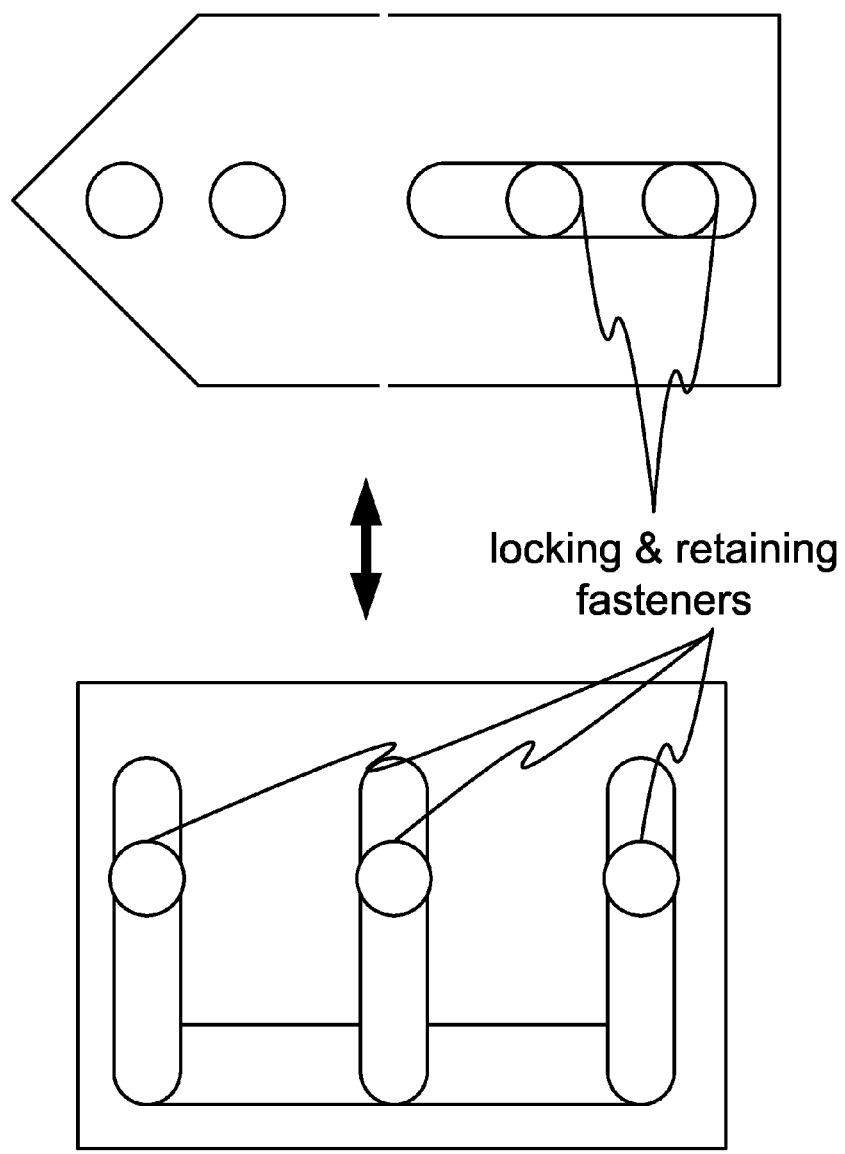
FIG. 6 shows the locking and retaining fasteners for the side plate attachment.

The design incorporates the following features for trouble-free implantation:

Lateral and vertical side plate adjustment incorporating ¼-½ turn locking and retaining fasteners (FIG. 6) that enables multiple positioning that accommodate a variable size range of patient anatomy. The side plates could be quickly adjusted before or during the surgery, therefore, reducing the operation time. FIG. 1 shows the slots (103) that are used for lateral adjustment of the side plates. There are typically 3 adjustment slots for each of the side plates as shown in FIG. 1 (103). FIG. 2 shows one of the side plates, which has vertical adjustment via a slot (206) and typically two screws (203).

Figure 7:
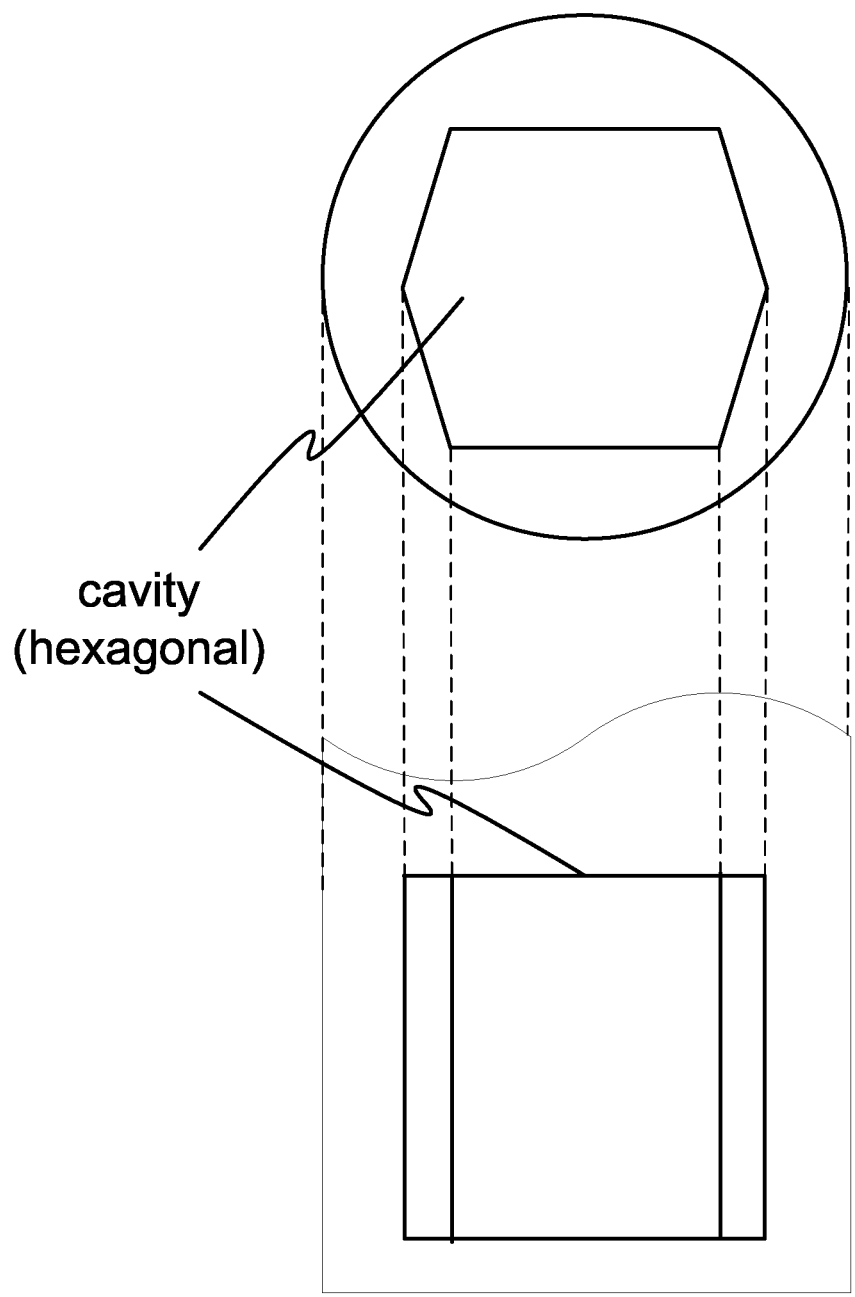
FIG. 7 shows the large bottom cavity of the implant body. This example shows a hexagonal shaped cavity.

An implant body that is capable of dual axis adjustment with a large cavity (FIG. 7) for multiple purposes, which include engaging the insertion handle, packing of bone graft material, and reducing the weight of the implant as shown in FIG. 3. The cavity has preferably an octagon or hexagon shape (301). The implant body may come in different diameter and lengths to accommodate different patient compositions. It could also be made of different materials that may include non-corrosive metals such as Titanium, plastic natural or man-made material.

The implant body design incorporates a stepped and pointed conical tipped end as shown in FIGS. 1 and 3 that promotes easier insertion into the patient (between the spinoud processes of the vertebrae in the lower back) and prevents excessive movement of the implant after surgery. The tipped end (102, 304) may be asymmetric for easier insertion.

Figure 8:
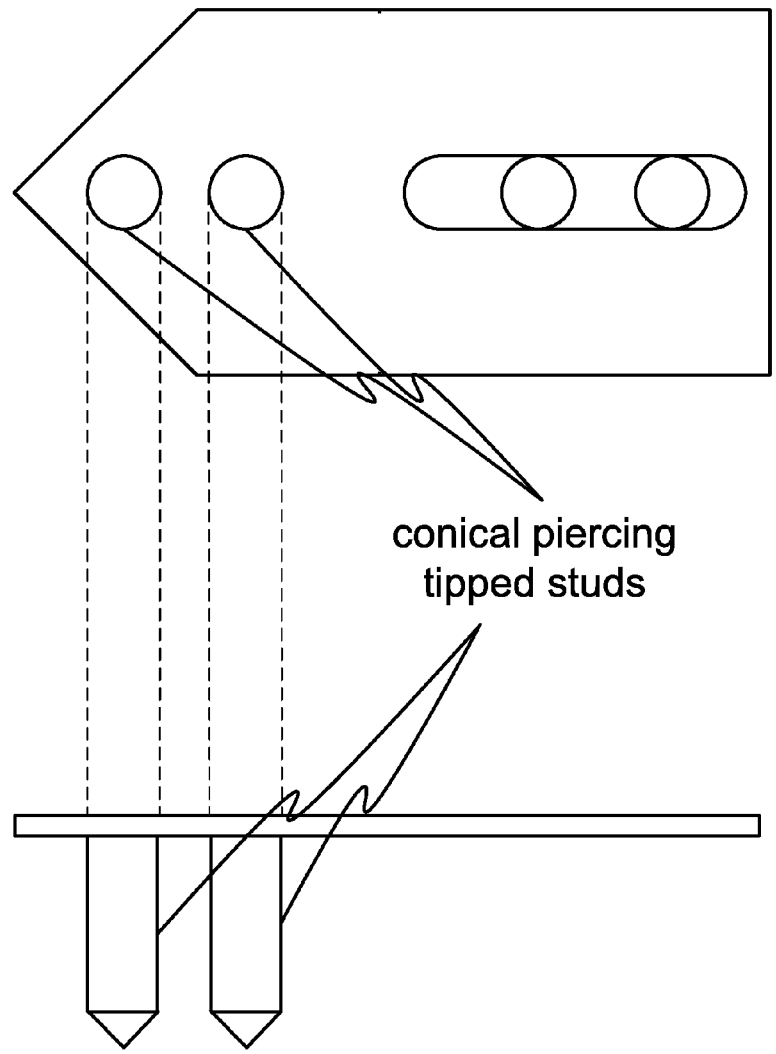
FIG. 8 shows the conical-shaped piercing tipped studs on the front and rear side plates

Conical piercing tipped studs (FIG. 8) on side plates for attachment to the vertebrae and therefore reducing the chance of the implant moving from its preferred spot shown in FIG. 2 (204, 205). Preferably two tipped studs are placed in the front (204) and two on the rear (205) of each side plate.

The implant design incorporates precision-machined slots and keys (103, 302, and 303) in the implant body and side plates to obtain a smooth running and sliding fit that prevent binding and allow for quick and easy adjustments in both lateral and vertical directions to accommodate a variety of patient compositions. The precision-machined slots allow for speedy and symmetrical installation of side plates, and therefore, reducing the operation time.

In one embodiment, the shape of the implant in 2 directions have 2 different cross-sections, one much larger, being asymmetric, making it ideal for locking and proper installation, for example, after rotation of the assembly by 90 degree, making sure that the device cannot be slide out (out of its intended position), for example, being locked at that direction, for proper and long-lasting installation in the body.

In one embodiment, the plates can be adjusted for multiple levels for vertebral body.

In another embodiment, the size is adjustable for different size patients, making it cheaper to manufacture, and easier to install, because it does not have to be custom-made much before the surgery, for each individual separately, based on his/her size and body structure.

Figure 11:
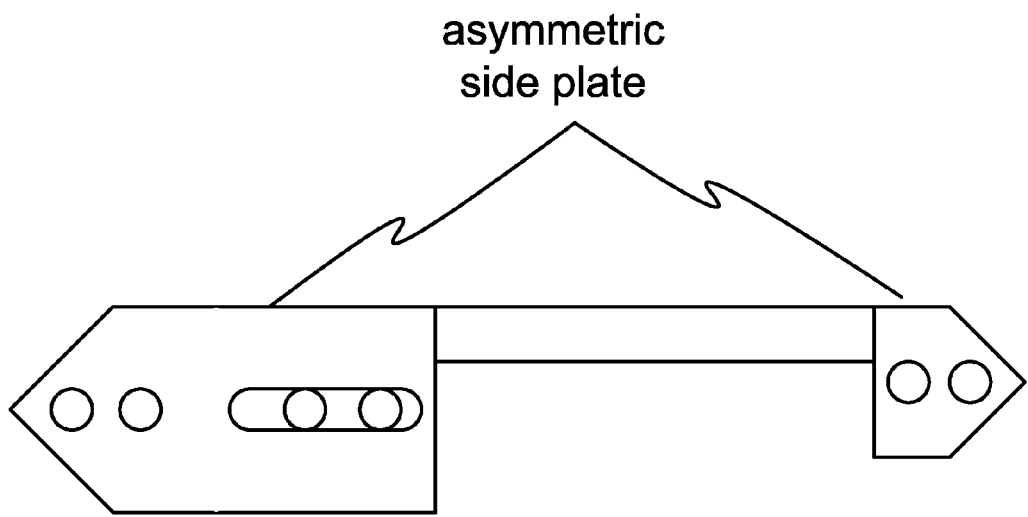
FIG. 11 shows an asymmetric side plate, with different front and rear wings sizes.

In one embodiment, the side plates are asymmetrical and the front and rear end of the side plates have different size (FIG. 11).

Figure 12:
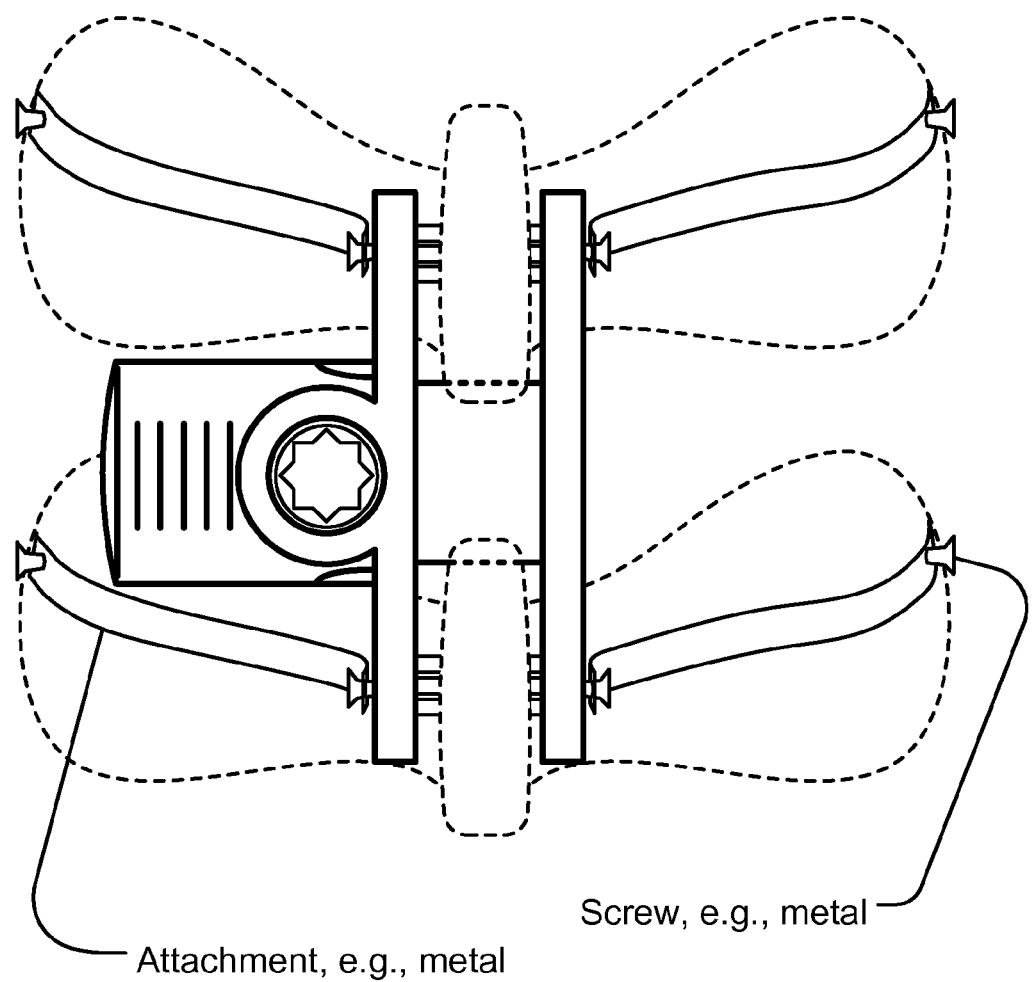
FIG. 12 shows the screws and bands that support the structure for one of the embodiments.
Figure 13:
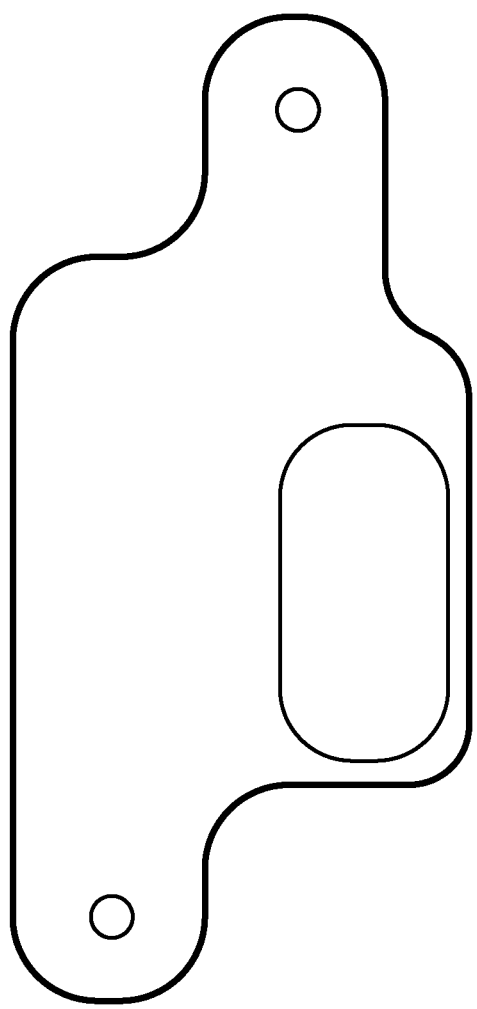
FIG. 13 shows the cross section or another view of the structure shown in FIG. 12.

More details are shown in the following figures: FIG. 12 shows the screws and bands that support the structure for one of the embodiments. FIG. 13 shows the cross section or another view of the structure shown in FIG. 12.

Note that easy installation means faster surgery, which means better survival rate after surgery.

Single Level Intra-Spinal Fusion:

The single level intra-spinal fusion is based on our multi-level intra-spinal fusion instrument. Like the multi-level fusion device, the single level consists of:

1. A sharp tip for easy insertion.
2. A rotational capability to help increase the space between the spinal process, e.g. between 2-5 mm.
3. A hollow canal to allow for increased and robust fusion in the spinal process.

In addition to allowing for successful execution of a single level intra-spinal fusion, this device can also be used for a facet fusion, specifically for patients with grade I and grade II spondyloisthesis. The device includes metal attachments that can be secured, via metal screws, from the fusion device itself, to the facet joint, permitting for successful facet fusion. See FIGS. 12-13 for details, in addition to appendices for more pictures and drawings. FIG. 12 shows the structure with metal (or other materials) bands (or arrays or series of bands) or stripes attached (slightly bended or curved for most configurations), holding or attaching or supporting the components, using two screws at the 2 ends (or similar attachment mechanisms).

Another Embodiment: 2-Piece or 3-Piece Configurations:

One embodiment of the present invention is a device with 2 or 3 pieces, with each piece with 2 clamps, symmetrically located on each side of each piece. The main piece has at least 2 screws which engage into 2 or more grooves in the side piece, to get attached to the side piece. The $3^{rd}$ piece, as an optional piece, is the bottom piece, which is similar to the side piece, and gets attached to the main piece, using same or different screws. Each piece is attached to the human body, during back surgery, with corresponding clamps.

In one embodiment, the materials used for clamps, pieces, and screws can be selected from a variety of composites, plastics, metal, alloy, and the like, which are durable, non-toxic, non-reactionary with the tissues (for allergy or rejection possibility by the body), reasonably priced, and/or easily manufactured. The clamps can be from the same materials as the pieces. The pieces may or may not be from the same materials. The clamps can be molded as one piece as the piece it is attached with.

In one embodiment, the configuration works with 2 pieces: the main piece and the side piece. In one embodiment, the configuration works with 3 pieces: the main piece, the side piece, and the bottom piece, which is more attached to the human body (with more number of clamps, at different positions).

Figure 14A:
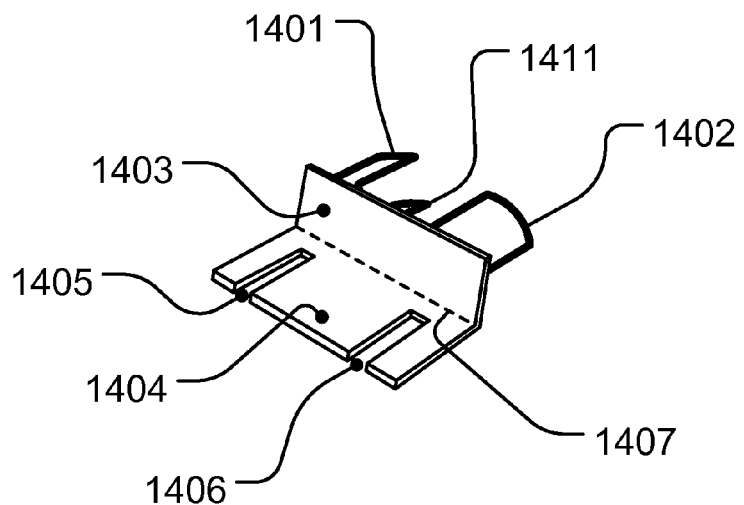
FIGS. 14a-b show an embodiment of the invention for the side piece (or the bottom piece), for 2 or 3-piece configurations, from 2 different views or perspectives, shown in 14(a) and 14(b).
Figure 14B:
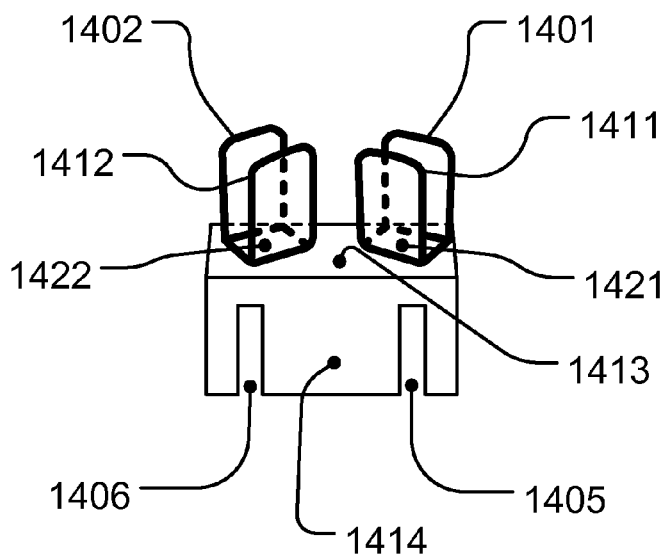

FIGS. 14a-b show an embodiment of the invention for the side piece (or the bottom piece), for 2 or 3-piece configurations, from 2 different views or perspectives, shown in 14(a) and 14(b). The components are: left clamp top finger (1401), left clamp bottom finger (1411), right clamp top finger (1402), right clamp bottom finger (1412), vertical plate front side (1403), horizontal plate front side (1404), left groove (1405), right groove (1406), bend line (1407), left clamp side (1421), right clamp side (1422), vertical plate back side (1413), and horizontal plate back side (1414).

Figure 15:
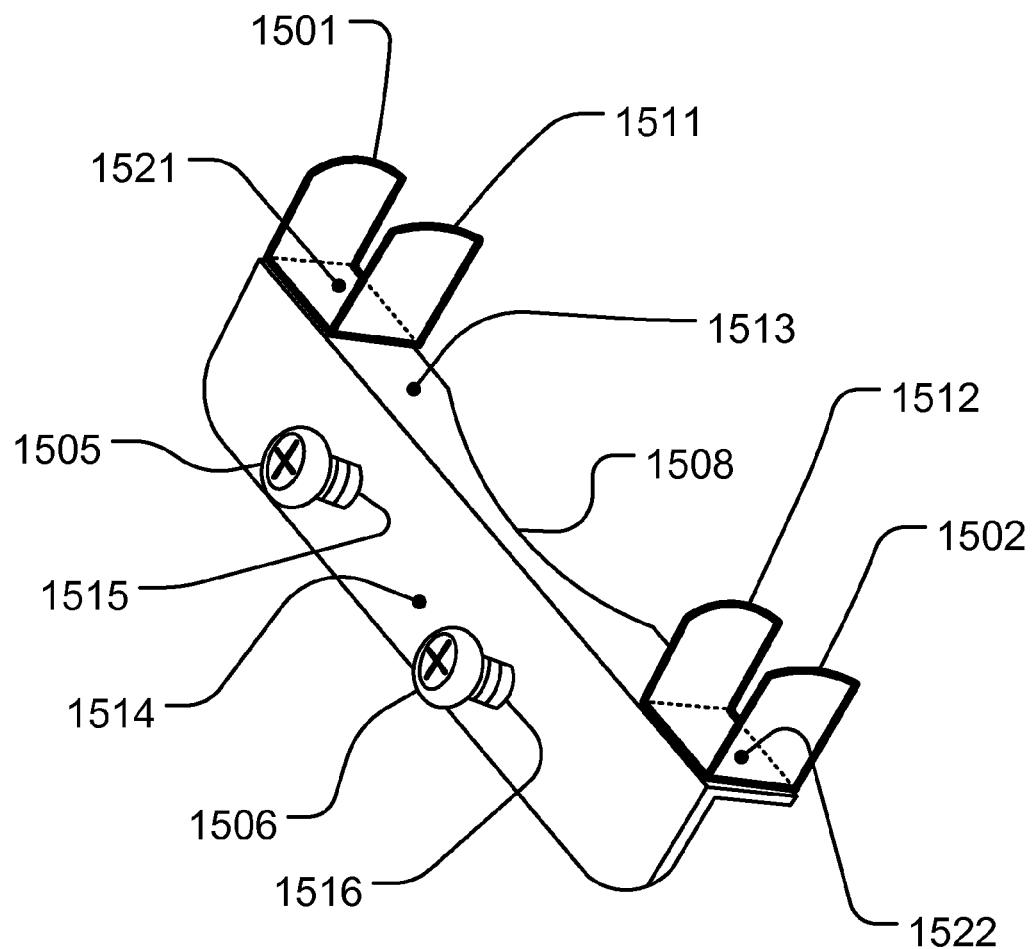
FIG. 15 shows an embodiment of the invention for the main piece (to be connected to the side piece and/or the bottom piece), for 2 or 3-piece configurations, with clamps and screws (or connectors).

FIG. 15 shows an embodiment of the invention for the main piece (to be connected to the side piece and/or the bottom piece), for 2 or 3-piece configurations, with clamps and screws (or connectors). The components are: left clamp left finger (1501), left clamp side (1521), left clamp right finger (1511), right clamp left finger (1512), right clamp side (1522), right clamp right finger (1502), bend line (separating plates 1513 and 1514), curved section (1508) to accommodate the body/bones/back, horizontal plate (1513) top side, vertical plate (1514) top side, left screw (1505), right screw (1506), left screw hole or position (1515), and right screw hole or position (1516).

Binders 1 and 2 (for 2 plus 6 figures, or for a total of 8 figures) describe or show the various examples and perspectives (pictures) of prototypes of this embodiment, from different angles, with 2-piece configuration (or optional 3-piece configuration), after surgery on the back, with respect to the back/bones, for humans.

In one embodiment, we have the side piece (FIG. 14) attached to the superior lamina (human back), using the 2 clamps (1401 and 1402), as shown in figures in Binders 1-2, and the main piece (FIG. 15) attached to facet joint (human back), using the 2 clamps (1501 and 1502), as shown in figures in Binders 1-2, for the 2-piece combination or configuration.

In one embodiment, we have the side piece (FIG. 14) attached to the superior lamina (human back), using the 2 clamps (1401 and 1402), as shown in figures in Binders 1-2, and the main piece (FIG. 15) attached to facet joint (human back), using the 2 clamps (1501 and 1502), as shown in figures in Binders 1-2, and the bottom piece (similar to FIG. 14) attached to the inferior lamina (human back), using the 2 clamps (similar to 1401 and 1402), for the 3-piece (optional) combination or configuration.

In one embodiment, we have the side piece sliding into the main piece, through the grooves 1406 and 1405, and secured with the screws 1505 and 1506. In one embodiment, we have the bottom piece sliding into the main piece, through the grooves similar to those of another 1406 and 1405, and secured with the screws 1505 and 1506, in addition to the above side piece, so that it attaches more to the body/back/human tissue.

This way, we can adjust on spot on different sizes of humans during surgery, not wasting time or resources or backup devices during or for surgery, which saves lives and money, as we can distract/open up the distances or gaps for different people or sizes, for the sliding part of the device above, as described in this embodiment, for 2-piece or 3-piece versions of the embodiment. The various versions of the arrangements and views of the devices on prototype models are shown in Binders 1-2, as Appendix/attached to this current disclosure.

The attachments with screws, holes, slots, and pins make the size adjustable for different patients and sizes. (This device or system can also be used for any animal for back surgery, for the same problem.)

Any material, such as plastic, titanium, alloy, metal, elastic, human tissue, animal tissue, cultured material, plant-based, oil-based, petrochemical, cotton, fabric, any byproducts, magnetic, non-magnetic, alloyed, plated, implanted, mix, powder, combination, mixture, and similar types, can be used.

The attachments can be done by screws, holes, slots, pins, ribbon, string, chain, cable, rings, human tissue, engineered tissue, glue, pressured material, Velcro-type, micro-sized devices, nano-fabricated material and devices, using only surface adhesion, using micro-property of materials, welded joints, hinges, locks, engagements devices, keys, and similar types.

Any variations of the above are also meant to be covered by the current patent application.

The invention claimed is:

1. An apparatus for decompressing spinal neuro elements, said apparatus comprising:
a side piece; a main piece; a bottom piece;
wherein said side piece comprises a first horizontal plate and a first vertical plate; a first clamp and a second clamp coupled to the first vertical plate; a first groove and a second groove positioned on the first horizontal plate;
wherein said bottom piece comprises a second horizontal plate and a second vertical plate; a fifth clamp and a sixth clamp coupled to the second vertical plate; a third groove and a fourth groove positioned on the second horizontal plate;
wherein said main piece comprises a third horizontal plate, and a third vertical plate;
wherein a third clamp and a fourth clamp coupled to the third horizontal plate; a first hole and a second hole positioned on the third vertical plate; wherein said third horizontal plate of said main piece comprises a curved section to accommodate human back;
wherein said first horizontal plate of said side piece slides onto said third vertical plate of said main piece; wherein said first horizontal plate of said side piece is securable to said third vertical plate of said main piece, using a first screw and a second screw, passing through said first groove and said second groove into said first hole and said second hole, respectively;
wherein said second horizontal plate of said bottom piece slides onto said third vertical plate of said main piece; wherein said second horizontal plate of said bottom piece is securable to said third vertical plate of said main piece, using said first screw and said second screw, passing through said third groove and said fourth groove into said first hole and said second hole, respectively;
wherein said side piece is attachable to a first spinal neuro element using said first clamp and said second clamp;
wherein said main piece is attachable to a second spinal neuro element using said third clamp and said fourth clamp;
wherein said bottom piece is attachable to a third spinal neuro element using said fifth clamp and said sixth clamp.

2. The apparatus as stated in claim 1, wherein said bottom piece is adjustable with respect to said main piece.

3. The apparatus as stated in claim 1, wherein said side piece is adjustable with respect to said main piece.

4. The apparatus as stated in claim 1, wherein third clamp and said fourth clamp are adjustable with respect to said main piece.

5. The apparatus as stated in claim 1, wherein said first clamp and said second clamp are adjustable with respect to said side piece.

6. The apparatus as stated in claim 1, wherein fifth clamp and said sixth clamp are adjustable with respect to said bottom piece.

7. The apparatus as stated in claim 1, wherein said apparatus comprises a third groove.

8. The apparatus as stated in claim 1, wherein said apparatus comprises a third hole.

9. The apparatus as stated in claim 1, wherein said apparatus comprises a third screw.

10. The apparatus as stated in claim 1, wherein said first horizontal plate and said first vertical plate are perpendicular to each other.

11. The apparatus as stated in claim 1, wherein said first horizontal plate and said first vertical plate are not perpendicular to each other.

12. The apparatus as stated in claim 1, wherein said second horizontal plate and said second vertical plate are perpendicular to each other.

13. The apparatus as stated in claim 1, wherein said second horizontal plate and said second vertical plate are not perpendicular to each other.

14. The apparatus as stated in claim 1, wherein said third horizontal plate and said third vertical plate are perpendicular to each other.

15. The apparatus as stated in claim 1, wherein said third horizontal plate and said third vertical plate are not perpendicular to each other.

16. The apparatus as stated in claim 1, wherein said bottom piece is made from metal, alloy, plastic, elastic, natural material, titanium, or man-made material.

17. The apparatus as stated in claim 1, wherein said side piece is made from metal, alloy, plastic, elastic, natural material, titanium, or man-made material.

18. The apparatus as stated in claim 1, wherein said main piece is made from metal, alloy, plastic, elastic, natural material, titanium, or man-made material.

19. The apparatus as stated in claim 1, wherein said first screw and said second screw are made from metal, alloy, plastic, elastic, natural material, titanium, or man-made material.

20. The apparatus as stated in claim 1, wherein said first clamp, said second clamp, said third clamp, said fourth clamp, said fifth clamp, and said sixth clamp are made from metal, alloy, plastic, elastic, natural material, titanium, or man-made material.

* * * * *